United States Patent [19]
Moorehead

[11] Patent Number: 5,984,902
[45] Date of Patent: Nov. 16, 1999

[54] OUTDWELLING SLIT VALVE AND VARIABLE CONTROL FOR CONTROLLING OPENING AND CLOSING THE SLIT

[75] Inventor: H. Robert Moorehead, Salt Lake City, Utah

[73] Assignee: Catheter Innovations, Inc, Salt Lake City, Utah

[21] Appl. No.: 09/039,620

[22] Filed: Mar. 16, 1998

Related U.S. Application Data

[62] Division of application No. 08/876,374, Jun. 16, 1997, Pat. No. 5,843,044.

[51] Int. Cl.⁶ ................................................. A61M 5/00
[52] U.S. Cl. ........................... 604/247; 604/248; 604/257; 137/845
[58] Field of Search ............................... 604/30, 31, 167, 604/246, 247, 256, 257; 137/524, 844, 845

[56] References Cited

U.S. PATENT DOCUMENTS

Re. 26,235  7/1967  Woodord ................................. 137/845
4,424,058  1/1984  Parsons et al. ........................ 604/118

Primary Examiner—Wynn Wood Coggins
Assistant Examiner—Deborah Blyveis
Attorney, Agent, or Firm—Foster & Foster

[57] ABSTRACT

An adjustable medical outdwelling, normally closed, pressure-responsive slit valve flow control for fluid (liquids and gases) and related methods wherein a diaphragm having a slit therein may be flexed both distally and proximally by respective pressure differentials across the diaphragm. One or more adjustment members are provided on one or both sides of the diaphragm to selectively adjust the amount of pressure differential required to open the slit valve.

12 Claims, 5 Drawing Sheets

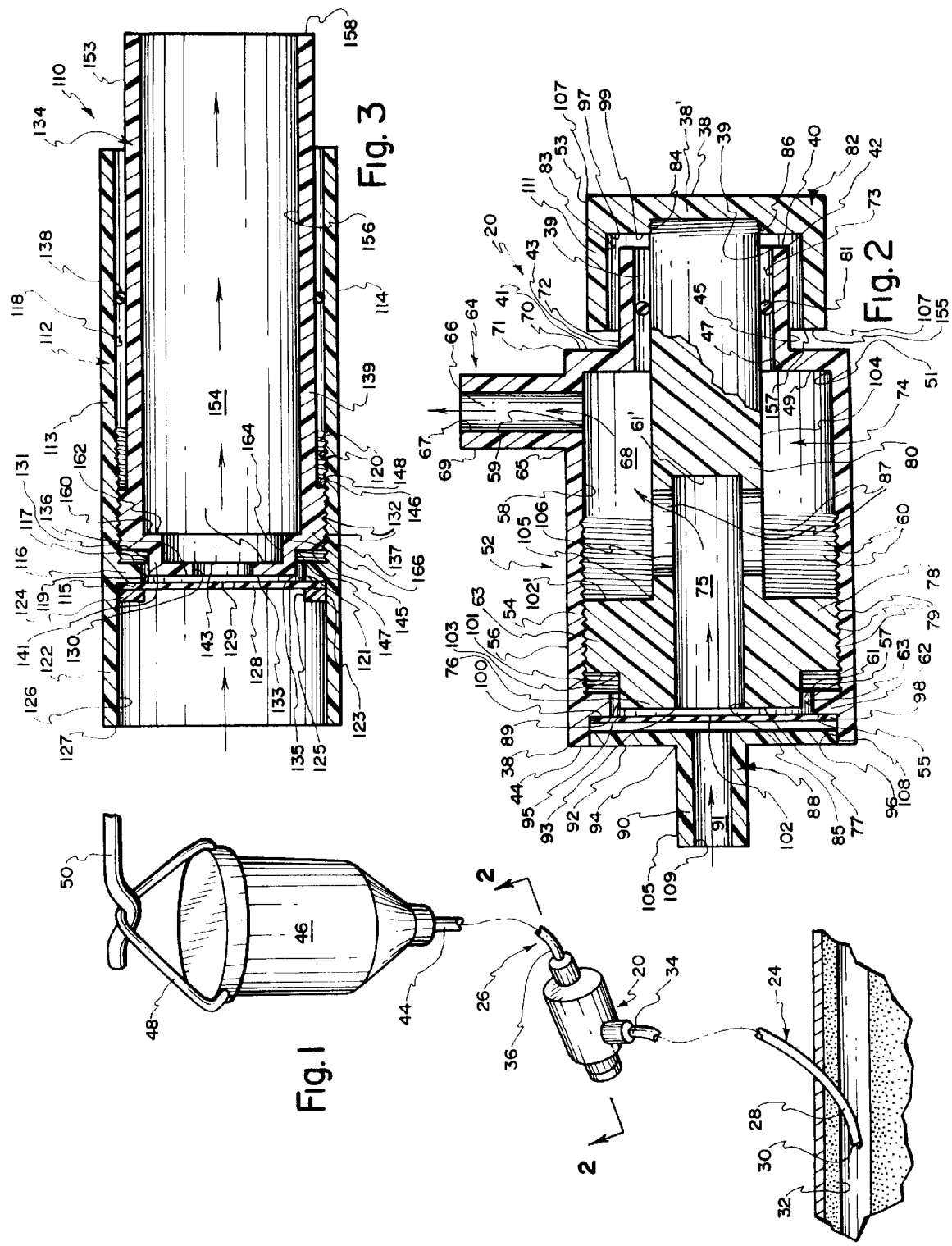

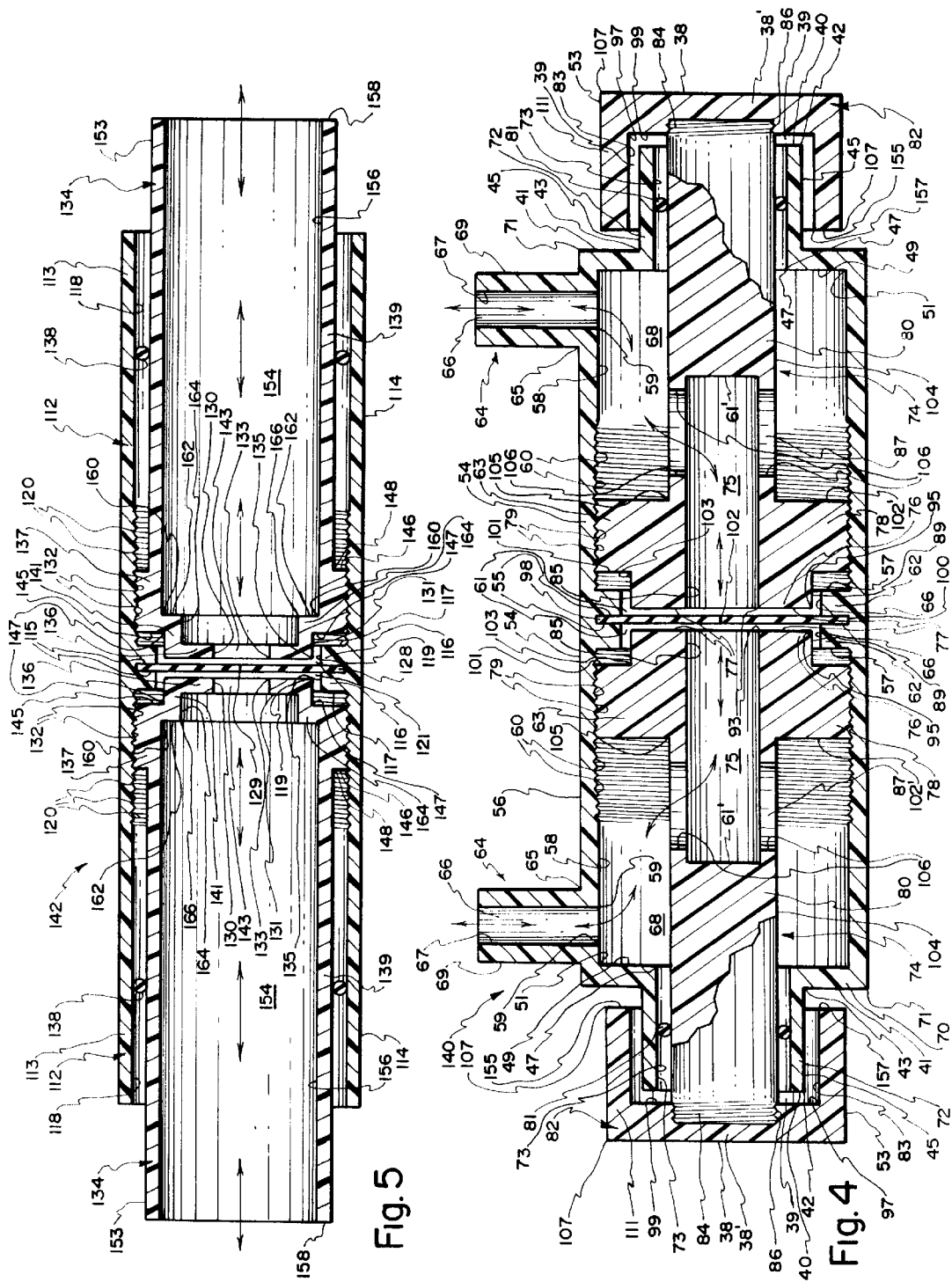

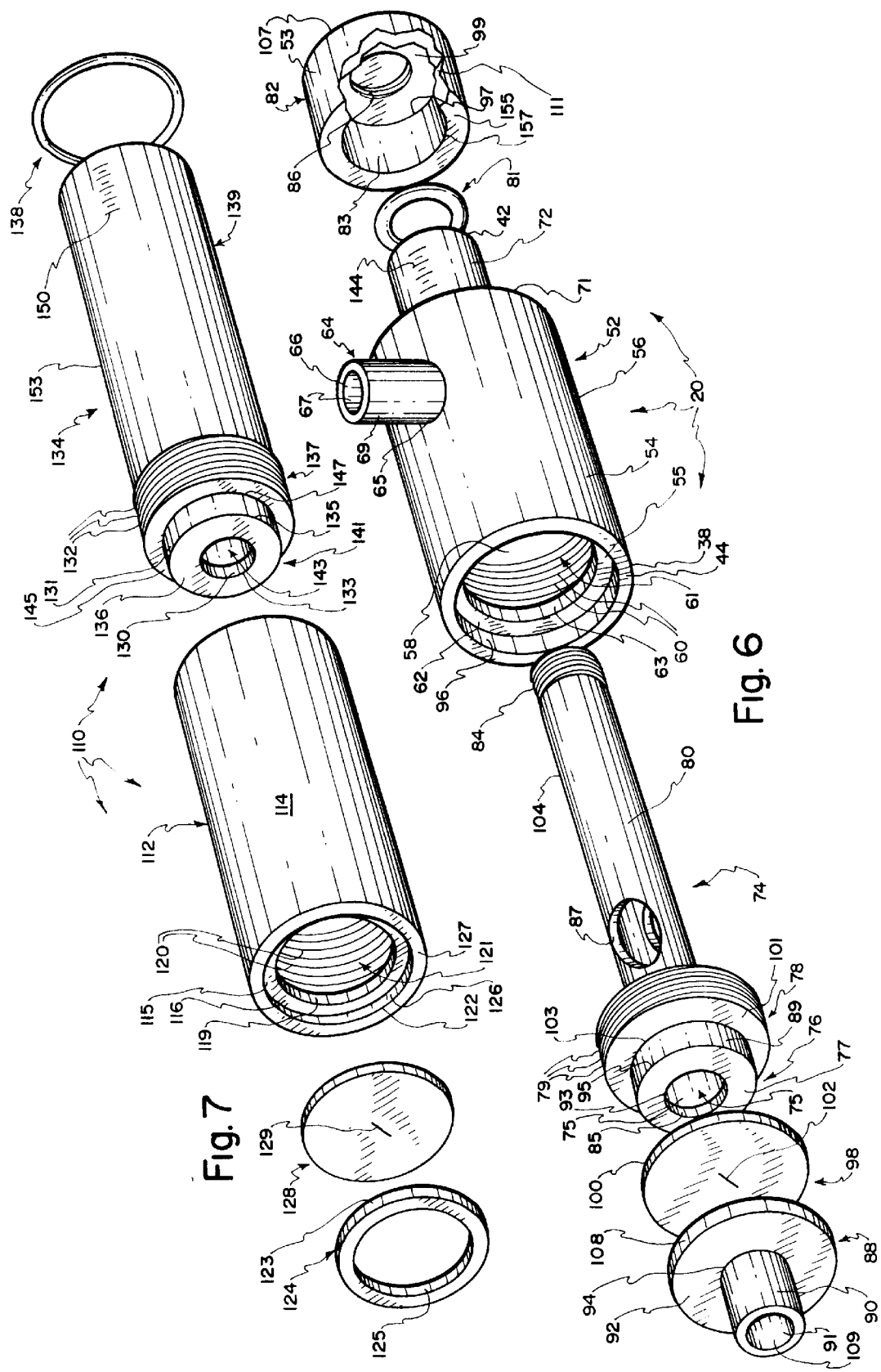

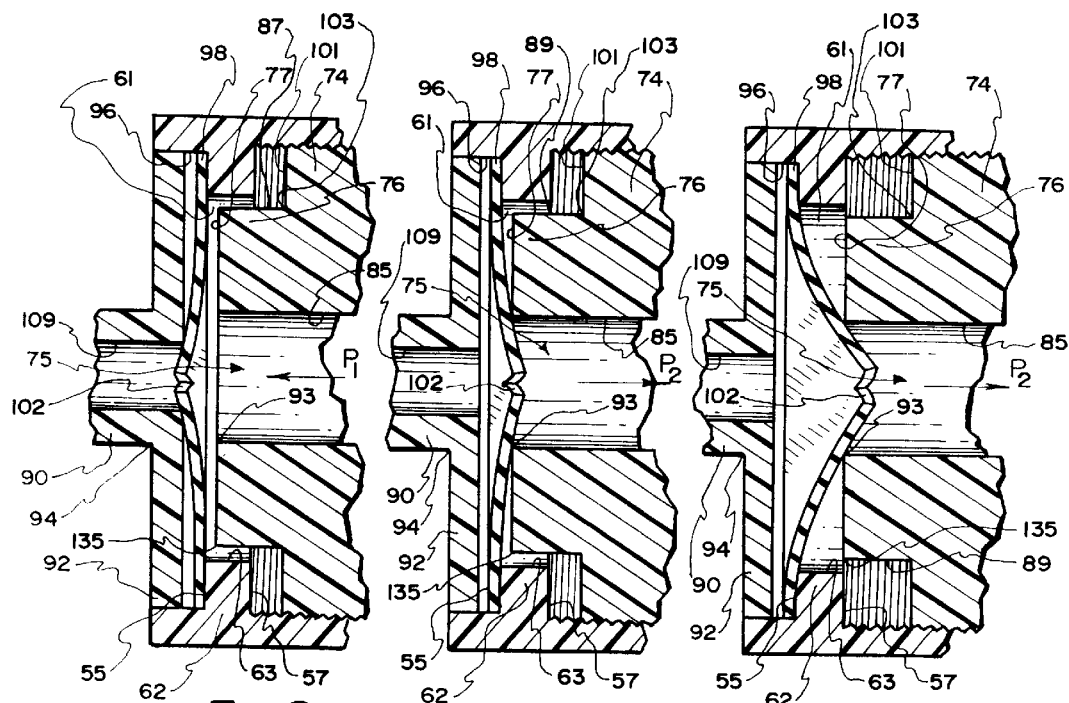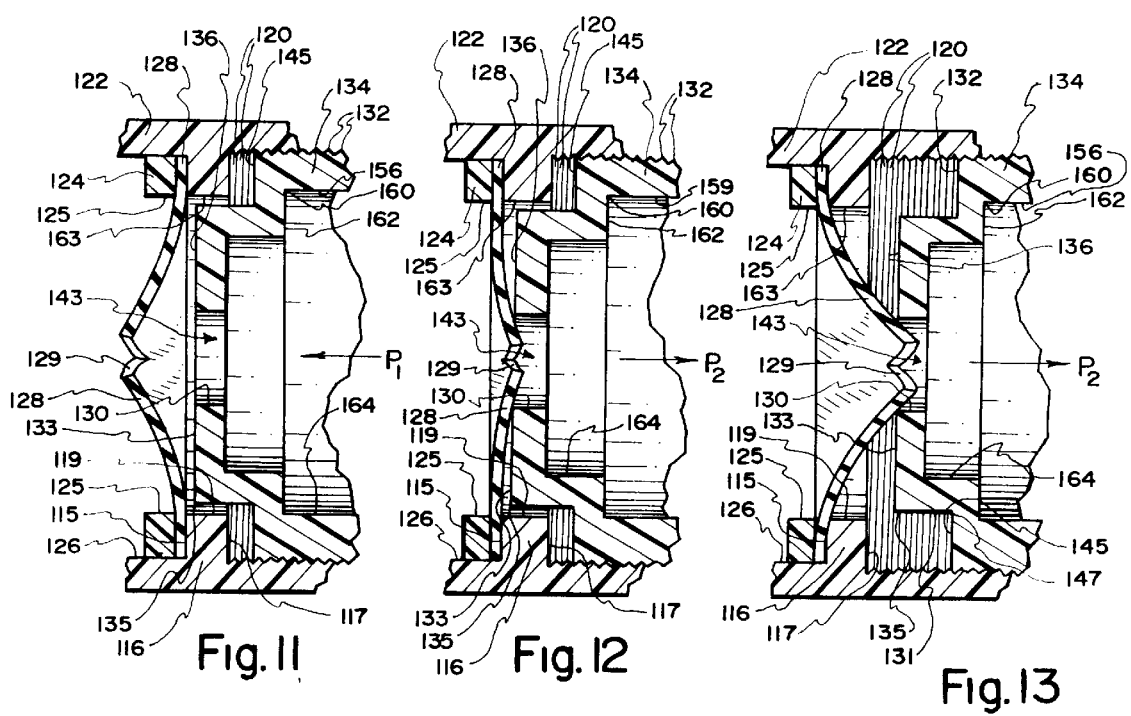

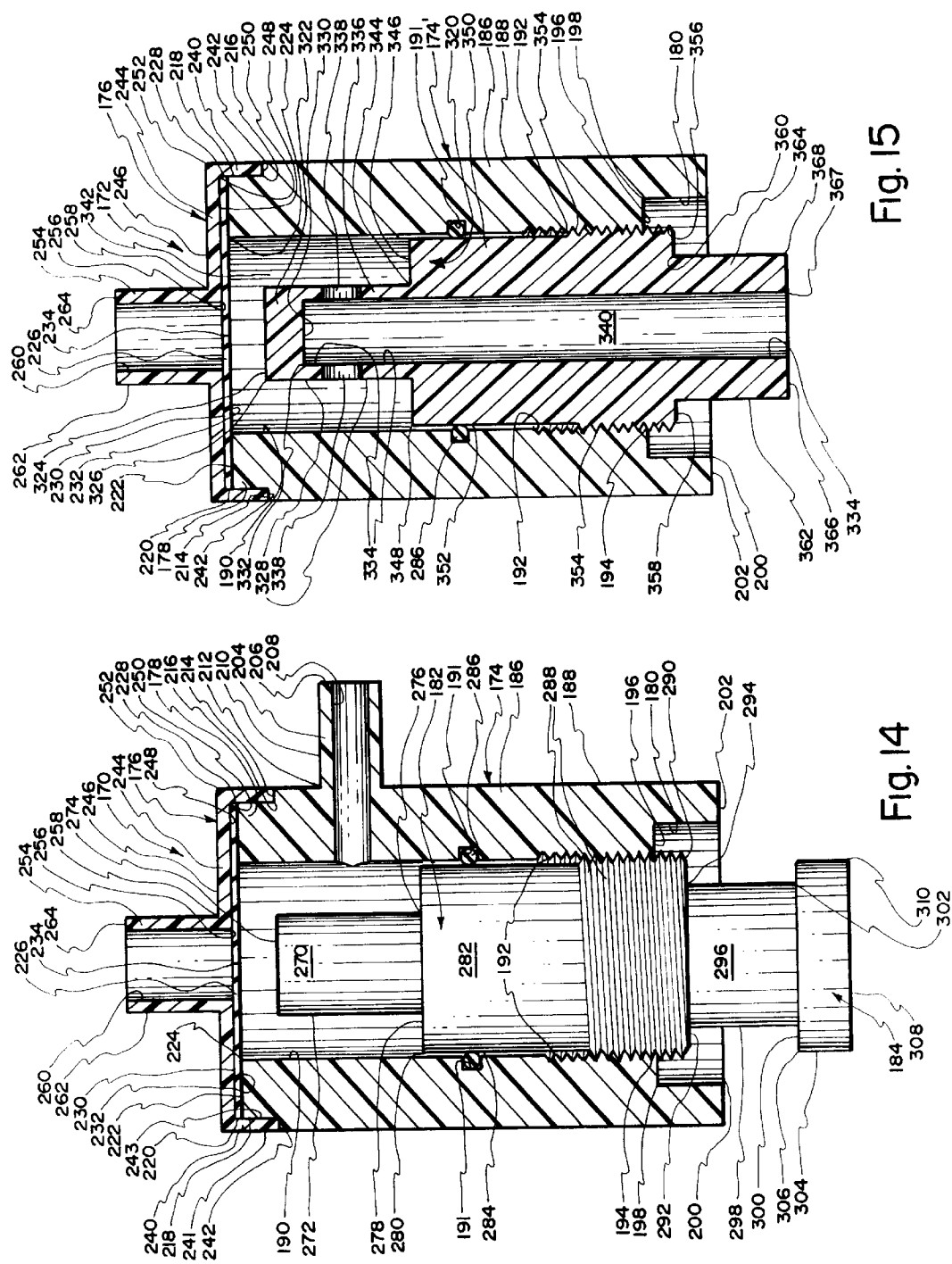

OUTDWELLING SLIT VALVE AND VARIABLE CONTROL FOR CONTROLLING OPENING AND CLOSING THE SLIT

This application is a division of my U.S. patent application Ser. No. 08/876,374, filed Jun. 16, 1997, now U.S. Pat. No. 5,843,044.

FIELD OF INVENTION

The present invention relates generally to improvement in the accuracy of medical liquid and gas flow control in a cannula, and more particularly to novel structure and methods for very accurate outdwelling selective slit valving of medical liquid flow, including a selectively settable control for varying pressure actuated thresholds and the degree to which the slit may open and close in one or both directions, the outdwelling slit valve being in association with a liquid-carrying cannula, such as a hollow catheter tube or needle, or, in the case of gas, a ventilating tube.

BACKGROUND

Valuable prior medical inventions pertaining to fluid flow (flow of liquids and gases) to and from a medial patient are acknowledged. Nevertheless, to some important extent, control of when and to what extent liquid and gas flow is permitted into and from a patient has been a long standing need in certain medical applications. Control of gas and liquid flow can be critical to the care for the patient. Flow of liquid to and from the patient includes but is not limited to infusion of intravenous liquid into the cardiovascular system and removal of blood samples. Flow of gas typically involves the respiratory system of the patient, including but not limited to preventing the patient from exhausting all gas within the lungs during exhalation, to thereby keep the air sacks in the lungs partially inflated and, therefore, continuously open. Control of gas and liquid flow can be critical to the care for the patient.

More specifically, in respect to liquid flow to the patient, it has long been recognized to be medically desirable to intravenously infuse a predetermined liquid into and to sample blood or other liquids from a patient. Typically, during delivery of IV solution to the patient through an infusion administration set comprising a cannula, such as a catheter tube or IV needle, it is difficult to accurately predict the point in time when the supply of IV solution will become exhausted. It is even more difficult to coordinate availability of nursing personnel to timely disable the IV administration set to prevent flow from a soon-to-be dry IV supply through the catheter tube or needle. As a consequence, the distal tip of the cannula sometimes experiences bleed-back and clotting. Also, as a container of IV solution progressively empties, a corresponding change in the hydraulic head takes place. As a consequence, a desired well regulated drip rate is not conventionally available.

More specifically, when a conventional IV administration set is connected to a patient, the flow of IV solution occurs because the force of gravity upon the solution in the elevated container exceeds the blood pressure in the cardiovascular system of the patient to the extent permitted by a manually-controlled drip mechanism. As the supply of IV solution is progressively used until exhausted, the pressure difference changes until there is no pressure component from the IV solution.

When the availability of IV solution is undesirably exhausted or low, the cardiovascular pressure prevails, causing blood flow into the IV catheter tube for a distance, which may vary depending on circumstances. Sometimes, this blood flow reaches, contaminates, and requires replacement of an IV filter, forming a part of the IV administration set. In any event, the aforesaid blood in the catheter will clot, within a short time. Subsequent negligent introduction of the clot into the bloodstream becomes a risk, which, if not discovered, places the patient at jeopardy. If timely discovered, replacement of the IV system is required.

Also, where the patient raises the venipuncture site above the IV container, refluxing or bleedback flow of blood into the distal end of the cannula sometimes occurs. This reflux may or may not reach the filter of the IV administration set, but, in either event, causes IV flow to stop, which results in clotting within either the cannula, the filter, or both. When and if discovered, both the clotted IV filter and catheter tube are replaced. This is disadvantageous because of accompanying patient trauma, expense, and risk. It is bad practice and an unacceptable risk to the patient to force a clot from the catheter tube into the bloodstream, but, due to negligence, this sometimes happens.

It is known to use a standard one-way outdwelling (outside the patient) valve to prevent undesired blood flow into the distal end of an indwelling cannula, such as a catheter tube or IV needle. This standard one-way valve will not allow blood sampling when the standard one-way valve is located between the catheter tube and the sampling site.

It has also been proposed that a two-way outdwelling slit valve (such as that disclosed in commonly owned U.S. Pat. No. 5,205,834) be used. With such a two-way outdwelling slit valve which has great medical value, the pressure requirements to open the slit valve are substantially fixed, i.e. built into the valve at the time of manufacture. The desired pressure requirement to open the slit valve in one direction of flow can be different than to open it in the other direction of flow.

Prior out-dwelling slit valves which are not readily adjustable, typically require a relatively high degree of manufacturing precision to ensure that the resulting valve opens in a given direction at the desired threshold.

In certain medical applications, it has been found desirable for outdwelling slit valves of the type disclosed in U.S. Pat. No. 5,205,834 be inventively extended into environments where the characteristics of the valves may be varied for control and adjustment purposes. For example. use of an outdwelling slit valve having variable characteristics in lieu of a mechanical drip controller, if inventively achieved would overcome or substantially alleviate the problems mentioned above concerning the IV administration sets.

Turning to flow of gases, proper respiratory care for the patient likewise requires precise control of the types and quantities of gases delivered to and expelled from the respiratory system of the intubated patient. When the patient is afflicted with some form of lung disease, the patient is typically placed on a respirator or ventilator. Sometimes controlled amounts of pure oxygen are cyclically delivered to the patient. Gas born medications are likewise sometimes introduced into the lungs on a controlled or metered basis. To prevent collapsing of the air sacks in the lungs, in the past, a C-PAP valve has been used to limit exhalation and prevent complete gas discharge from the lungs.

Reliability and precision of gas flow control devices, such as the C-PAP valve, for use with the respiratory system of a patient have presented persistent problems. Almost constant or regular intermittent overseeing has often been required by a medical provider in order to insure that errors and malfunction of such prior art gas flow control devices do not work adversely to the best interests of the patient.

There has long existed a need for a gas flow control which is precise, reliable, and unlike the present C-PAP valves, for example, does not require substantial on-going monitoring by a nurse or other medically trained person.

BRIEF SUMMARY AND OBJECTS OF THE INVENTION

In brief summary, the present invention overcomes or substantially alleviates problems of the prior art and extends valuable outdwelling slit valve technology into the variable characteristics realm for significant medical purposes. Novel outdwelling, normally-closed, pressure-responsive medical slit valve assemblies are provided for controlling certain types of flow of liquid and gas to and from a patient where flow characteristics can be selectively varied. Each slit valve assembly comprises a readily adjustable control to selectively set and alter the pressure differential threshold or thresholds at which the slit valve opens and closes in one or both directions and the degree of flexure accommodated. Related methods are also provided. In certain embodiments of the invention, the control may be characterized as a diaphragm flex adjustment mechanism. Thus, in accordance with the present invention, the pressure requirements necessary to open the slit of the valve in a given direction can be quickly varied, as medically appropriate. Accordingly, the present invention provides novel slit valve mechanisms, and related methods, each valve mechanism comprising a control by which flow characteristics thereof in one or both directions can be selectively, immediately, and conveniently altered.

With the foregoing in mind, it is a primary object of the present invention to overcome or substantially alleviate problems associated with prior art medical liquid and gas flow controls for flow liquid and/or gas to and/or from a medical patient.

Another object of importance is the provision of a two-way slit valve, and related methods, which comprise an adjustable control by which the flow characteristics thereof in directions are selectively and conveniently altered.

A further paramount object is the provision of a two-way outdwelling slit valve wherein the flow characteristics thereof can be selectively varied.

It is an object of considerable value to provide an outdwelling slit valve mechanism wherein the degree of flexure of a flexible diaphragm is selectively restricted by an adjustable control.

It is another dominant object to provide a two-way outdwelling valve structure of relatively simple design and is adjustable to alter the flow characteristics thereof.

It is another object of significance to provide a normally-closed adjustable outdwelling slit valve, the flow characteristics of which can be changed.

A further valuable object is the provision of an outdwelling slit valve control for use in an IV administration set to control the IV drip.

A further paramount object is the provision of normally closed outdwelling slit valve mechanisms comprising selectively settable controls for changing the flow/non-flow characteristics thereof.

Another important object is the provision of an adjustable outdwelling slit valve wherein the internal gas or liquid flow adjacent the slit is either generally axial or is diverted and non-axial in whole or in part or some of both.

It is another valuable object to provide an outdwelling threshold adjustable slit valve which can be used to control respiratory gas flow in respect to a medical patient.

An additional dominant object is the provision of a normally closed slit valve for use in lieu of a C-PAP valve to prevent full discharge of gas from the lungs of an intubated patient.

These and other objects and features of the present invention will be apparent from the detailed description taken with reference to the accompanying drawings.

BRIEF DESCRIPTION OF THE DRAWINGS

FIG. 1 is a perspective of one adjustable, outdwelling, two-way, normally closed, pressure-responsive slit valve liquid flow control embodying the principles of the present invention, shown in an installed condition as part of an IV administration set;

FIG. 2 is an enlarged cross section, taken along lines 2—2 of FIG. 1 having both generally axial and diverted non-axial internal liquid flow, usable, for example, in conjunction with the cardiovascular system of a medical patient;

FIG. 3 is a cross section of a normally closed valve structure embodying principles of the present invention wherein the proximal and distal ingress and egress ports for gases are in direct alignment and internal gas flow is generally axial, usable, for example, to prevent full discharge of gas from the lungs of a patient;

FIG. 4 is a cross section similar to FIG. 2 but depicting a normally closed valve structure embodying principles of the present invention comprising control features for adjusting and regulating liquid flow bi-directionally and having both generally axial and diverted non-axial internal liquid flow;

FIG. 5 is a cross section similar to FIG. 3 of a normally closed valve structure embodying principles of the present invention comprising control features for adjusting and regulating gas flow bi-directionally where internal gas flow is generally axial;

FIG. 6 is an exploded perspective of the valve structure of FIG. 2;

FIG. 7 is an exploded perspective of the valve structure of FIG. 3;

FIG. 8 is an enlarged, fragmentary cross section showing the central slit of diaphragm of the valve assembly of FIG. 1 flexed left into an open condition by a threshold pressure differential $P_1$;

FIG. 9 is an enlarged fragmentary cross section showing the central slit of the diaphragm of the valve assembly of FIG. 1 flexed right into an open condition by a threshold pressure differential $P_2$, the flexure of the slit diaphragm being partially constrained by the adjustable control;

FIG. 10 is an enlarged fragmentary cross section similar to FIG. 9 with the adjustable control spaced a greater distance from the diaphragm accommodating a greater flexure to the right of the slit in the diaphragm;

FIG. 11 is an enlarged, fragmentary cross section of the slit valve of FIG. 3 flexed open to the left due to pressure differential $P_1$ with the control closely spaced from the diaphragm;

FIG. 12 is an enlarged, fragmentary cross section of the slit valve of FIG. 3 flexed open to the right due to pressure differential $P_2$, the flexure of the slit diaphragm being partially constrained by the control, which is closely spaced from the diaphragm;

FIG. 13 is an enlarged, fragmentary cross section similar to FIG. 12 of the slit valve of FIG. 3 flexed open to the right due to pressure differential $P_2$, the flexure of the slit diaphragm being less constrained than in FIG. 12 with the control spaced a greater distance from the diaphragm;

FIG. 14 is a longitudinal cross section of a further selectively settable outdwelling slit valve assembly accommodating diverted internal flow; and FIG. 15 is a longitudinal cross section of still another selectively settable outdwelling slit valve assembly accommodating diverted internal flow.

DETAILED DESCRIPTION OF THE ILLUSTRATED EMBODIMENTS

Reference is now made to the drawings wherein like numerals are used to designate like parts throughout. FIGS. 1, 2, and 6 illustrate one configuration of an adjustable, pressure responsive, outdwelling slit valve and control mechanism or assembly in accordance with principles of the present invention. This embodiment is specifically designed for use with the cardiovascular system of a medical patient. FIGS. 3 and 7 illustrate a second configuration of an adjustable slit valve control mechanism or assembly in accordance with principles of the present invention. This embodiment is specifically designed for use with the respiratory system of a medical patient. FIGS. 4 and 5 illustrate two additional adjustable valve embodiments which enable bi-directional adjustment of the pressure requirement of the slit valve control mechanism or assembly. FIGS. 8 through 13 illustrate various control settings and the effect of different pressure differentials across the slit diaphragm, while FIGS. 14 and 15 illustrate further embodiments of the invention having control-diverted internal flow.

Valve assembly 20 is illustrated in FIG. 1 (as part of an IV administration set) in an operational or "as used" liquid control condition, i.e. here the slit valve assembly 20 is operatively interposed between a cannula in the form of a catheter tube, generally designated 24, and an IV tube, generally designated 26. It is to be appreciated that the IV administration set use depicted in FIG. 1 is only exemplary in that the present invention contemplates adjustable outdwelling slit valve control for selective delivery of liquid or gas to and from appropriate internal locations within a medical patient.

The catheter tube 24, illustrated in FIG. 1, may be of any available type and is illustrated as having a distal end portion 28 comprising a distal port 30 placed indwelling in the cardiovascular system of a medical patient, namely in the patient's vein 32. The catheter tube 24 comprises a proximal end portion 34, illustrated as being force-fit into or otherwise suitably positioned in liquid communicating relation with one part of the adjustable slit valve assembly 20.

Likewise, tube 26 may be of any desired type by which outdwelling medical liquid is selectively made available to the slit valve assembly 20. Tube 26 is illustrated as comprising a distal end portion 36 which may be force-fit into or otherwise suitably positioned in liquid communicating relationship with the adjustable slit valve assembly 20 at the other port thereof.

FIG. 1 further illustrates IV tube 26 as comprising a proximal end 44, which is illustrated as being suitably connected to an IV bottle 46 (shown suspended by a bracket 48 from a cantilevered support arm 50), all of which is conventional. Thus, for example, IV solution in bottle 46 is selectively and controllably passed through valve assembly 20 at a desired rate into the vein 32 via catheter tube 24, responsive to pressure imposed by a hydrostatic head.

With reference to FIGS. 2, 6, and 8 through 10, the adjustable slit valve control assembly 20 will now be described in greater detail. The adjustable slit valve control assembly 20 is shown as generally comprising an externally exposed housing 52, an adjustment or control member 74, an exposed handle 82, a gasket or seal 81, a slit diaphragm 98, and a male connector element 88.

While housing 52 may be formed of any suitable material, the housing is illustrated as being formed of medical grade synthetic resinous material or plastic. Housing 52 comprises a relatively large annular or cylindrical wall 54, shown as being generally of uniform thickness and comprising a cylindrical exterior surface 56 and a concealed inner surface 58 which defines an internal cavity 68. Advantageously, an annular retention wall or inwardly directed radial flange 62 interrupts inner surface 58 and comprises a first radial surface 55, a second radial surface 57, and an annular orifice-defining edge surface 63 within which an aperture 61 (FIGS. 8 through 10) is formed. The diameter of the surface 63 is shown as being less than that of the inside diameter of the wall 54 housing at surface 58. Threads 60 are formed on part of the housing inner surface 58, which threads commence immediately adjacent to and extend away from the annular retention wall or flange second surface 57. The purpose and function of the threads 60 and the annular retention wall or flange 62 will be hereinafter more fully explained.

The cylindrical exterior surface 56 of housing 52 is interrupted by a cylindrical liquid flow port defining boss 64. The boss 64 is shown as being hollow and formed as one piece with and oriented substantially perpendicularly to the longitudinal axis of housing 52. Boss 64, comprises a boss exterior surface 69 and a hollow interior 66, defined by a boss inner surface 67, through which liquid selectively flows. The boss exterior surface 69 interrupts and merges with exterior surface 56 at exterior annular corner 65. Similarly, the boss inner surface 67 intersects the housing interior surface 58 at interior annular corner 59. As illustrated, the hollow interior 66 is in direct open communication with the housing internal cavity 68.

The cylindrical exterior surface 56 intersects at one end with annular edge surface 44 of housing 52 at exterior annular corner 38. At the other end thereof, exterior surface 56 merges with radial surface 41 of annular shoulder 70 at exterior annular corner 71. Similarly, housing inner surface 58 intersects with the shoulder interior surface 49 at annular interior corner 51.

A reduced diameter or stepped cylindrical extension 72 of housing 52 extends from the annular wall 70 and comprises interior surface 73 and exterior surface 45 and is illustrated as being hollow, cylindrical, and formed as one piece with the housing 52. The interior surface 73 defines a hollow cylindrical interior 39 and is shown as comprising a diameter substantially less than the diameter of the housing inner surface 58. As shown, the interior surface 73 intersects with inner surface 49 at annular corner 47. Likewise, the exterior surface 45 intersects with the shoulder exterior surface 41 at annular exterior corner 43. The wall 72 terminates at blunt edge 40 which intersects the interior surface 73 at annular interior corner 39 and exterior surface 45 at annular exterior corner 42. The housing extension wall 72 is shown as being aligned or coaxial with the housing 52.

To adjust the pressure differential requirement necessary to open the slit diaphragm 98, the adjustment member or variable control 74 is adjustably disposed within housing 52. The adjustment member 74 is illustrated as having a threaded end 84, an elongated portion 80, an enlarged threaded portion 78 comprising threads 79 and a contact or abutment extension 76. The contact extension 76 is shown as comprising an annular ring which comprises a cylindrical inner surface 85, an exterior surface 89, and a radial contact surface 77. The contact surface 77 is oriented perpendicularly to and intersects with the inner surface 85 at annular corner 93 and with the exterior surface 89 at annular exterior corner 95. The interior surface 85 defines hollow portion or chamber 75 through which liquid selectively flows. As best illustrated in FIG. 2, hollow portion 75 extends from surface 77 of the contact extension 76 a substantial distance into the elongated portion 80, terminating at flat surface 61.

The enlarged diameter threaded portion 78 is illustrated as being formed adjacent to contact extension 76. Enlargement 78 is shown as being formed as one piece with the contact extension 76 and the elongated portion 80 of the adjustment member 74 and as comprising front wall surface 101 and rear wall surface 102. Wall surfaces 101 and 102 are shown as being substantially perpendicular to contact extension exterior surface 89. Wall surface 101 intersects with contact extension surface 89 at annular exterior corner 103. Similarly, wall surface 102 intersects with an exterior surface 104 of the elongated portion 80 at annular exterior corner 105. Annular threads 79 are formed on the threaded portion 78 between walls 101 and 102. The diameter of the threaded portion 78 and the make-up of threads 79 are such that proper threaded engagement with housing threads 60 and adjustment member threads 79 occurs, as shown in FIG. 2.

In the assembled, operable condition shown in FIG. 2, the adjustment member threads 79 are threadedly engaged by the threads 60 formed on the housing inner surface 58. With such engagement of threads 79 and 60, the longitudinal position of adjustment member 74 within the housing 52 can be selectively set or varied by manually rotating the adjustment member or control 74 relative to the housing 52.

Additionally, to prevent leakage of liquid from between the adjustment member 74 and the housing extension 72, a gasket 81 or seal in the form of an O-ring is disposed between the surface 104 and the surface 73. The gasket or O-ring 81 is compression-fit between the surfaces 104 and 73.

The elongated portion 80 of the adjustment member 74 has two opposed transverse apertures 87 which extend transversely through the elongated portion 80 between the hollow interior 75 and the cavity 68. Each transverse aperture 87 is defined by a cylindrical surface 106 to permit fluid communication between the chamber 75 and the cavity 68.

As shown, the adjustment member 74 also comprises a handle or knob 82 into which the threaded end 84 of the adjustment member 74 is non-rotatably secured to accommodate manual relocation of the adjustment member 74 within the housing 52. The handle 82 is shown as comprising a blunt transverse end wall comprising outer surface 38' and inner surface 99. The surface 99 comprises a threaded blind bore 86 to receivingly accept threaded end 84 of the elongated portion 80 in non-rotatable relation. The blunt end wall 38' merges as one piece with cylindrical wall 111 to form a cup-shaped member. Wall 111 comprises cylindrical interior surface 83 and cylindrical exterior surface 53 and is shown as being of uniform thickness. Cylindrical interior surface 83 joins annular front surface 99 at annular corner 97. The handle front surface 53 and surface 38 intersect at annular corner 107. The cylindrical exterior surface 53 provides a suitable gripping location from which a user may selectively rotate the handle 82 clockwise or counterclockwise and thus rotate the adjustment member 74. Such manual adjustment will alter the pressure at which the slit 102 in the diaphragm 98 will open to the right as shown in FIG. 2 and will change the amount of space between the diaphragm 98 and surface 55, without requiring the valve assembly 20 to be disconnected or disassembled. Surface 53 may be knurled or otherwise made to accommodate a secure manual grip.

The male connector 88 comprises a planar base 92 which is radially disposed and comprises outer edge 108. A flow port defining annular boss 90 is shown as being formed as one piece with the planar base 92 and extends outwardly from the planar base at annular corner 94 in an axial direction. The annular boss 90 has an exterior surface 105 and an interior flow path-defining surface 109, which surrounds a hollow interior 91 therein. In the assembled configuration illustrated in FIG. 2, the connector edge 108 is sealed and secured within annular housing 52 at interior surface 96. The connector 88 may be secured within the inner surface 96 by bonding agent, adhesion, press-fit attachment, or in any other suitable way.

In the assembled configuration illustrated in FIG. 2, the slit diaphragm 98 is interposed between the connector 88 and the annular retention wall 62. The diaphragm is contiguous with flange 62, but spaced at surface 55 from base 92. The slit diaphragm 98 is disk-shaped and advantageously formed of a suitable elastomeric material, such as silicone rubber. Silicone rubber offers the advantage of ease in accommodating controlled centrally flexing of the diaphragm and has good memory characteristics. The diaphragm 98 is illustrated in FIG. 2 in an unstressed condition. Diaphragm 98 is planar and of uniform thickness, comprising peripheral edge 100, the unstressed diameter of which is slightly less than the diameter of the inner surface 96.

Diaphragm 98 further comprises the centrally-disposed, normally-closed, transversely-directed linear slit 102. Slit 102 is illustrated as uniformly extending through diaphragm 98 and is located along the longitudinal access of the valve assembly 20 so as to be directly aligned with hollow interiors 91 and 75, when assembled. The radial length of slit 102 is selected to accommodate the desired range of distal and proximal flexing in order to accommodate selective bidirectional liquid flow through the flexed and opened slit 102 to introduce, for example, IV solution into the patient under hydrostatic IV pressure or to remove sample blood from the patient under negative pressure or to introduce medication into the bloodstream. In addition to the length of the slit 102, the material used to form the diaphragm 98, the thickness of the diaphragm, and the respective diameters of the previously described, hollow interiors 75 and 91 individually and collectively are variables to be set by those knowledgeable in the art in determining the range of pressure differentials by which the slit 102 is caused to be opened by flexing distally and proximally.

The outdwelling fluid control devices according to the present invention can be freestanding, for addition to a cannula, such as a catheter or a needle, at the time of use or can be constructed as a component part of an IV cannula system at the time of manufacture.

In operation, as illustrated in FIGS. 8 through 10, as the contact surface 77 is moved closer to the slit diaphragm 98 by rotation of the control 74 in respect to the housing 52, the flexure of the slit diaphragm becomes increasingly restricted in the direction of the contact surface 77. For example, in FIG. 9, as pressure differential $P_2$ acts on the slit diaphragm 98, the slit diaphragm 98 is caused to flex from left to right. However, as shown, such flexure is restricted by the contact surface 77 of the adjustment member 74 engaging the slit diaphragm 98. Accordingly, when the flexure of the slit diaphragm 98 is so restricted, a pressure differential $P_2$ of a greater magnitude is required in order to cause the slit valve to be flexed sufficiently to open the slit 102 than when the slit diaphragm is permitted to flex without restriction. Thus, when the contact surface 77 is moved farther from the unstressed position of the slit diaphragm 98, for example as shown in FIG. 10, the slit diaphragm 98 is less restrained and to a greater extent thereby spreading the lips of the slit 102 a greater distance apart when subjected to pressure differential $P_2$. This accommodates a larger rate of flow through the slit 102 from left to right.

While FIGS. 9 and 10 illustrate the slit diaphragm 98 being opened in one direction (toward the right) due to pressure differential $P_2$, the slit diaphragm 98 may also be opened in the opposite direction by pressure differential $P_1$, as illustrated in FIG. 8. In contrast with the opening of the slit diaphragm from left to right as illustrated in FIGS. 9 and 10 (based upon the selective setting of control 74) the pressure requirement to open the slit diaphragm, 98 in a direction away from the adjustment member or control 74 is not per se adjustable because the position of base 92 is fixed in respect to the diaphragm 98.

Liquid flow across the diaphragm 98 when slit 102 is open in either direction is generally axial on both sides of the diaphragm 98. However, the flow between chamber 75 and cavity 68 is somewhat radial or transverse and the influent or effluent into and from cavity 68 is radial or transverse within the boss 64.

FIGS. 3 and 7 illustrate another embodiment of the invention, designed to control gas flow, namely an adjustable slit valve control mechanism 110 which also permits adjustment in the gas pressure threshold or differential required to open the valve mechanism 110. The adjustable slit valve control mechanism 110, as shown, comprises a hollow cylindrical housing 112, an adjustment member or manual control 134, a slit diaphragm 128, a retainer 124, and an O-ring seal or gasket 138.

Housing 112 is illustrated as comprising a cylindrical wall 113 comprising exterior surface 114 and an inner surface 118. The interior surface 118 is interrupted by an annular retention wall or flange 116 formed as one piece with the wall 113. The annular retention wall or flange 116 extends radially inwardly and comprises a front radial surface 115, a rear radial surface 117, and an interior edge surface 119. The interior surface 119 defines an aperture or orifice 121, the diameter of which is shown as being less than the diameter of the housing interior surface 118.

Also illustrated as being formed as one piece with the housing wall 113 are internal threads 120. The housing threads 120 are shown as commencing at a location adjacent to annular surface 117 and extending a significant distance along the housing interior surface 118 from left to right as viewed in FIG. 3. The purpose and function of the housing threads 120 will be hereinafter more fully explained.

The housing 112 comprises a cylindrical wall segment 122, extending from right to left from flange 116 and comprising an extension of wall 113. Wall segment 122 is illustrated as being formed as one piece with the rest of housing 112. The extension or wall segment 122 is hollow, of uniform thickness, and comprises an inner surface 126. Extension 122 terminates at blunt, radially-directed edge 127.

In the assembled condition illustrated in FIG. 3, slit diaphragm 128 is contiguous at its periphery with surface 115 of inwardly-directed flange 116. A retainer ring 124 is positioned within the annular housing extension 122 to be peripherally contiguous with the opposite side of the diaphragm 128. This secures the slit diaphragm 128 within the housing 112 between the retainer ring 124 and the retention flange 116. The retainer ring 124 comprises an interior edge surface 125, an exterior edge surface 123, and is illustrated as being of uniform thickness. The diameter of the interior surface 125 is shown as being approximately the same as the diameter of the surface 119. The diameter of the retainer ring outer surface 123 is illustrated as being approximately the same as the diameter of the annular housing extension inner surface 126. The retaining ring may be secured within the housing extension 122 by a bonding agent or adhesion, a press-fit relationship plastic welding, or in any other suitable way.

Slit diaphragm 128 is shown as being compressively interposed between retention wall 116 and retainer 124 against separation. The slit diaphragm 128 comprises slit 129 formed centrally therein and has the type of the characteristics and features described above in connection with slit diaphragm 98. Accordingly, no further description of the slit diaphragm 128 is necessary.

Adjustment member or control 134 is threadedly disposed within the housing 112 so as to be co-axial therewith. The adjustment member 134 is illustrated as comprising an enlarged threaded portion 137, an elongated cylindrical wall portion 139, and a contact extension, nose portion or abutment wall 141. The contact extension 141 comprises an inwardly-directed radial-oriented annular ring which comprises an annular orifice-forming interior surface 130, and flat surface 131, a peripheral edge surface 131' and a diaphragm contact surface 136. The contact surface 136 is illustrated as being oriented perpendicularly to and intersecting with the interior surface 130 at annular corner 133 and with the peripheral surface 131' at annular corner 135. Interior surface 130 defines aperture 143 through which liquid selectively flows.

As best illustrated in FIG. 2, aperture or orifice 143 extends axially through the contact extension 141 into elongated portion interior cavity 154, which is defined by interior surface 156 of wall 139. The interior surface 156 extends from annular blunt edge 158 of wall 139 to annular corner 160 where interior surface 156 intersects interior annular shoulder surface 162. As shown, the annular shoulder surface 162, which is radially oriented, intersects the cylindrical interior extension surface 164 of wall 164' at corner 166.

The enlarged diameter threaded portion 137 is illustrated as being adjacent and connected to contact extension 141 by wall 164'. The threaded portion 137 is shown as being formed as one piece with the contact extension 141, wall 164' and elongated portion 139 of the adjustment member 134. The threaded portion 137 comprises radially-directed front wall surface 145 and radially-directed rear wall surface 146. Wall surfaces 145 and 146 are illustrated as being substantially perpendicular to the longitudinal axis of valve assembly 110. Wall surface 145 intersects with contact extension surface 131' at annular corner 147. Similarly, wall surface 146 intersects with the exterior surface 153 of the elongated portion 139 at annular corner 148. Threads 132 are formed on the enlarged diameter threaded portion 137 between walls 145 and 146 and are oriented so as to be parallel with the housing inner surface 118.

The diameter, size, shape, location, and orientation of the adjustment member threads 132 are such that the proper, adjustable, threaded engagement between housing threads 120 and adjustment member threads 132 occurs, as shown in FIG. 3. With such engagement of threads 132 and 120, the longitudinal position of adjustment member 134 within the housing 112 can be selectively changed by manually rotating the adjustment member 134 clockwise or counter clockwise relative to the housing 112.

To prevent pneumatic leakage of liquid between the exterior surface 153 of the elongated portion and the housing interior surface 118, O-ring 138 is disposed therebetween. As illustrated in FIG. 3, the O-ring type gasket 138 is compression-fit between the exterior surface 153 and the surface 118.

A primary function of the adjustment member contact surface 136 is to selectively be engaged by the slit diaphragm 128. Contact surface 136 selectively restricts flexure of the slit diaphragm 128 in the direction of the contact surface 136. Adjustment of the space between the diaphragm 128 and surface 136 (via rotation of control 134), adjusts the pneumatic pressure requirement necessary to open the slit 129 of diaphragm 128. This is illustrated in FIGS. 12 and 13. In FIG. 12 the contact surface 136 is closer to the slit diaphragm 128 and, therefore, the flexure of the slit diaphragm 128 in the direction of the contact surface 136 becomes increasingly restricted.

For example, in FIG. 12, as pressure differential $P_2$ acts on the slit diaphragm 128, the slit diaphragm 128 is caused to flex, by in a restricted way, in the direction of the pressure differential. As stated, the flexure is restricted by rapid engagement of the diaphragm 128 with the contact surface 136 of the adjustment member 134. Accordingly, when the flexure of the slit diaphragm is so restricted, a pressure differential of a greater magnitude is required in order to cause the slit diaphragm 128 to be flexed sufficiently to open the slit 129 than when the flexure slit diaphragm 128 is unrestricted, or less restricted. In contrast, as shown in FIG. 13, when the adjustment member 134 is moved farther from the unstressed, closed position of the slit diaphragm 128, the slit diaphragm 128 may be more substantially flexed sufficiently to open by a predetermined pressure differential, of significantly less magnitude than the pressure differential required to open the slit diaphragm 128 when restricted as shown in FIG. 12.

As illustrated in FIG. 11, slit diaphragm 128 may also be opened at slit 129 by flexure in a direction away from adjustment member 134 due to an oppositely directed pressure differential $P_1$ of predetermined threshold magnitude. The location of control 134 is essentially immaterial when the pressure differential is toward the left as in FIG. 11. Because in FIG. 11 there is an adjustment member 134 disposed on only one side of diaphragm 128, the pressure requirement to open the slit diaphragm in a direction away from the adjustment member is not per se adjustable.

To controlling the amount of pressure required to open the valve in either direction, an adjustment member or control may be placed on each side of the slit diaphragm. In this way, the dual controls may be used to selectively adjust the amount of pressure required to open a slit diaphragm in either direction. In FIGS. 4 and 5, adjustable slit valve assemblies are illustrated which accommodate bi-directional flow and bi-directional pressure requirement adjustment are illustrated. As is readily apparent, the left and right hand sides of the valve assembly embodiments of FIGS. 4 and 5, respectively comprise mirror images on opposite sides of the slit diaphragm of embodiments illustrated in FIGS. 2 and 3, respectively, and described above. Due to the substantial identity, features of the embodiments illustrated in FIGS. 4 and 5 are designated with the same numerals as corresponding features illustrated in FIGS. 2 and 3, respectively. The embodiment of FIG. 4 was designed to bi-directionally variably control liquid flow while the embodiment of FIG. 5 was designed to bi-directionally variably control gas flow.

Referring to FIG. 4, bi-directional pressure requirement adjustment valve control assembly 140 is illustrated as comprising a single housing which comprises two oppositely extending housings 52 formed as one piece two opposed adjustment members 74 are oppositely adjustably disposed one in each of housings 52. Interposed between adjustment members 74 is slit diaphragm 98, which is secured between the two annular retention walls 62. One of the cylindrical liquid flow port defining bosses 64 is communicably attached to a catheter tube 24 while the other is attached to an IV tube 26 (as illustrated in FIG. 1). Due to the structural and operational identity between the two halves of the embodiment of FIG. 4 and the above-described embodiment of FIG. 2, no further structural description of the FIG. 4 embodiment is necessary.

In operation, the pressure requirements necessary to open slit diaphragm 98 of bi-directional valve control assembly 140 can be selectively adjusted in any desired way, for example, so that, in each direction, they are different. To increase the pressure differential necessary to open the slit diaphragm 98 by flexing the slit diaphragm in the left-hand direction as shown in FIG. 4, the adjustment member 74 on the left-hand side is displaced closer to the slit diaphragm 98, thereby increasing the degree of restriction of the silt diaphragm flexure in the left-hand direction. Advantageously, the adjustment member 74 is brought closer to the slit diaphragm 98 by rotating the adjustment member 74 relative to the housing 52, so that the adjustment member 74 can threadedly advance longitudinally in respect to housing 112.

Similarly, if it is desired to reduce the pressure differential requirement necessary to open the slit diaphragm 98 of valve 140 by flexing it in the left-hand direction, the adjustment member 74 on the left-hand side is moved away from slit diaphragm 98 so as to reduce or eliminate the amount of restriction of the flexure of the slit diaphragm 98 in the left-hand direction, thereby permitting the slit diaphragm 98 to be opened by flexure in the left-hand direction by a lesser pressure differential than when the contact surface 77 is disposed near the slit diaphragm. As explained earlier, similar adjustments can be made on the right-hand side of valve control assembly 140 to adjust the pressure differential requirement necessary to open the slit diaphragm by flexure in the right-hand direction.

Accordingly, by selective adjustment of the adjustment members 74, with respect to the slit diaphragm 98, the pressure differential requirement necessary to open the slit valve in either the left-hand or the right-hand direction or both can be easily adjusted. Moreover, the valve control 140 can be adjusted so that the pressure requirement necessary to open the slit valve in one direction is different from the pressure requirement necessary to open it in the other direction. For example, if it is desired that the pressure requirement to open the slit diaphragm 98 by flexure in the left-hand direction be greater than the pressure requirement necessary to open the slit diaphragm in the right-hand direction, then the adjustment member 74 on the left-hand side is positioned closer to the slit diaphragm 98 than the adjustment member 74 on the right-hand side. Thus, so configured, the flexure of the slit diaphragm 98 in the left-hand direction will be more restricted than the flexure in the right direction and a greater pressure differential therefore will be needed to open the slit valve in the left-hand direction than in the right-hand direction, assuming adjustment member inside surfaces 85 have equal diameters.

As stated above, FIG. 5 illustrates a yet further pneumatic embodiment of the present invention. Specifically, FIG. 5 illustrates bi-directional pressure requirement adjustable valve assembly 142. As discussed above, the left-hand side of valve control assembly 142 comprises a mirror image of the adjustable flow control mechanism 110 of FIG. 3 taken about the slit diaphragm 128. Accordingly, both left and right-hand features of the valve control assembly 142 are designated with the same numerals as the same features in FIG. 3, already described. Due to the structural identity between each of the two halves of the embodiment of FIG. 5 and the embodiment of FIG. 3, no further structural description of the structural features of the FIG. 4 embodiment is necessary.

As illustrated, the valve control assembly 142 comprises two adjustment members or controls 134 movingly disposed within a housing 112 on opposite sides of a slit diaphragm 128. The slit diaphragm 128 is shown as being peripherally secured between two retention walls 116 integrally formed on the housing inner surface 118. To prevent leakage from the valve control 142, O-ring gaskets 138 are provided between adjustment member exterior surface 153 and housing interior surface 118.

In a manner similar to that of the embodiment shown in FIG. 4A valve control assembly 142 permits bi-directional adjustment of the pressure requirement necessary to open the slit diaphragm 128 in either direction by selectively varying flexure available to the slit diaphragm using the adjustment members 134. The hollow interior of one of the adjustment members 134 is liquid communicably attached to a ventilating tube, while hollow interior of the other adjustment member 134 is liquid communicably attached to a respiratory tube. To increase the pressure differential required to open the slit diaphragm 128 by controlling the degree of flexure available in the left-hand direction, the adjustment member 134 on the left-hand side is moved closer to the slit diaphragm 128. The adjustment member is brought closer to the slit diaphragm 128 by threadedly rotating adjustment member 134 relative to housing 112, so that adjustment member 134 is threadedly advanced longitudinally through housing 112. In the same way, flexure of the slit diaphragm 128 is restricted in the right-hand direction as well. To increase the pressure requirement necessary to open the slit 129 of the slit valve 128 by flexure in the right-hand direction, the adjustment member 134 on the right-hand side is moved closer to the slit diaphragm 128. Thus, the diaphragm more rapidly engages the member 134, which restricts its flexure in the right-hand direction, thus requiring a greater pressure differential in the right-hand direction to open the slit valve than would be the case if the adjustment member 134 were spaced a greater distance from the diaphragm 128.

Flow control valve assembly 142 may be adjusted so that the pressure requirements to open the slit valve in the left-hand direction are different from the pressure requirements necessary to open the slit diaphragm 128 in the right-hand direction. This is done by selectively placing the left and right-hand adjustment members at different distances from the slit diaphragm 128.

To assist in adjusting valve structures or assemblies formed in accordance with the present invention, markings may be advantageously provided to enable measurement of the relative positions of the various adjustment members within the housings and relative to the slit diaphragms of the various embodiments. This is advantageous due to the valve control feature that the relative positions of an adjustment member and a slit diaphragm define a pressure differential necessary to open the slit valve in a given direction. By measuring these relative positions, the user is able to selectively choose a desired pressure differential by adjusting the relative positions of the slit diaphragm and the adjustment member to predetermined positions.

Such markings or indicia are illustrated in FIGS. 6 and 7. In FIG. 6, markings 144 are provided on the housing extension 72 to permit the user to gauge the position of the handle 82 relative to the housing extension 72. Similarly, in FIG. 7, markings 150 are provided on the adjustment member 134 external surface to permit the user to gauge the position of the adjustment member relative to the housing 112.

An inspection of FIGS. 2 through 13 makes it clear that the embodiments depicted therein, which embrace principles of the present invention, accommodate generally axially-directed liquid or gas flow adjacent to each side of the slit valve diaphragm. In the case of the embodiments of FIGS. 3 and 5, the flow on each side of the diaphragm is generally axially directed and is not diverted. In the case of the embodiments illustrated in FIGS. 2 and 4, the axial flow adjacent to one side of the diaphragm is within a chamber of the control or adjustment member. This chamber flow is diverted from the axial into a somewhat transverse and circuitous path within the associated valve housing and ultimately is radial or transverse flow at ports 66.

Reference is now made to FIGS. 14 and 15, which respectively illustrate two further slit valve/control assemblies, generally designated 170 and 172. While the embodiments of FIGS. 14 and 15 are specifically for variable control of liquid flow, the same basic principles of the present invention apply to variable control of gas flow. In each of these two embodiments, flow on the control side of the diaphragm is diverted in more or less a radial direction adjacent to the diaphragm and circuitously beyond that, all within the interior of the valve assembly. In other words, linear flow directly into the control or adjustment member adjacent to the diaphragm is prohibited and the control serves not only to vary the pressure differential threshold for opening of the slit in the diaphragm in the direction of the control, but as a flow diverting member as well.

With specific reference to FIG. 14, assembly 170 comprises a cylindrical housing, generally designated 174. Tubular housing 174 carries an end cap, generally designated 176, at one end 178 thereof. The other end of the cylindrical housing 174 comprises an annular opening 180 through which a diaphragm threshold control/flow diverting member, generally designated 182, is inserted into the hollow interior of the cylindrical housing 174 during assembly. Threshold control/flow diverter 182 comprises a manual knob 184 by which the position of the control/diverter 182 may be axially varied within the hollow interior of the cylindrical housing 174.

Housing 174 comprises a cylindrical wall 186. Wall 186 comprises a cylindrical or annular exterior surface 188, illustrated as being of uniform diameter throughout. Wall 186 also comprises a smooth cylindrical or annular interior surface 190 of a predetermined diametral size. Internal surface 190 is interrupted by a groove 191 and includes threads 192 adjacent to annular opening 180. Threads 192 merge at corner 194 with a radially-directed surface or shoulder 196. Shoulder 196 merges at corner 198 with annular surface 180. Annular surface 180 merges at annular corner 200 with a blunt end edge 202 of wall 186.

The exterior surface 188 is interrupted at a predetermined location by a radially-directed boss 204. Boss 204 comprises a cylindrical wall which terminates at a blunt edge 206, defines a hollow flow path at interior cylindrical surface 208 and comprises an exterior cylindrical or annular surface 210. Annular surface 210 merges with surface 188 at annular inside corner 212.

The forward end 178 of wall 186 is stepped at shoulder 214 to a reduced diametral size. Shoulder surface 214 merges at corner 216 with cylindrical surface 218. Cylindrical surface 218 merges at corner 220 with blunt, radially-directed end surface 222 of wall 186. Edge surface 222 merges at outside corner 224 with the hollow interior cylindrical surface 190.

A flat diaphragm 226 is contiguously superimposed upon blunt end surface 222 near the periphery of the diaphragm 226. The diaphragm 226 is illustrated as being formed of suitable elastomeric material, such as silicone rubber, and is circular or disk-shaped in its configuration. Diaphragm 226 comprises peripheral edge 228, which is compressively held against inadvertent release, opposed radially directed surfaces 230 and 232, and a central slit 234 of predetermined length. Slit 234, in its closed position comprises opposed lips which are contiguous one with the other.

The diaphragm 226 is compressively secured in its contiguous relation with surface 222 by end cap 176. End cap 176 comprises an annular, axially-directed wall 240, which comprises an end edge surface 242 sized and shaped so as to be flush with surface 214. Annular wall 240 comprises a thickness substantially the same as the radial length of wall 214, the thickness being illustrated as uniform throughout wall 240. Wall 240 comprises an exterior annular surface 241 and an interior surface which is bonded, glued, or plastic welded to surface 218. Wall 240 merges with radially-directed annular wall 244, which is illustrated as being of uniform thickness and as comprising opposed radially directed surfaces 246 and 248. Wall 244 is illustrated as merging as one piece with wall 240 at inside and outside corners 250 and 252.

Radially-directed annular wall 244 is interrupted by axially-directed boss 254. Boss 254 comprises a cylindrical wall which merges at corners 256 and 258 with wall 244. Cylindrical wall 254 is illustrated as being of uniform thickness comprising interior cylindrical surface 260 and exterior cylindrical surface 262. Wall 260 defines a liquid flow path on one side of the diaphragm 226. Wall 254 terminates in blunt end edge surface 264.

Bosses 204 and 254 are sized and shaped to receive, in a compression fit relationship, tubing through which liquid selectively flows in the manner illustrated and described in conjunction with FIG. 1.

As can be seen from observance of FIG. 14, cylindrical housing 174 and end cap 176 are separately formed from the suitable medical grade synthetic resinous material in accordance with the exercise of skill by artisans in the field.

It is to be appreciated that flow occurs selectively across the diaphragm 226, i.e. only when the slit 234 is caused to be opened responsive to a predetermined pressure differential (net pressure). The flow is between the internal chambers defined by the hollow cylindrical surfaces 208 and 260, respectively, of bosses 204 and 254.

As mentioned earlier, control/diverter 182 is secured against inadvertent removal from housing 174, but is axially adjustable in respect to housing 174 in a manner and for purposes hereinafter more fully described. Control/diverter 182 is generally cylindrical and is stepped in its external configuration. The distal cylindrical portion 270 comprises a cylindrical surface 272, the diametral size of which is substantially smaller than the diameter of surface 190, but larger than the diameter of surface 260. Distal cylindrical end 270 of control/diverter 182 is illustrated as being internally solid and comprises a blunt, impervious, radially directed distal end surface 274. Surfaces 272 and 274 serve, among other functions, to divert liquid flow into a stepped pattern between the boss passageways defined by surfaces 208 and 260.

Cylindrical surface 272, which is axially directed, merges at annular inside corner 276 with an outwardly-directed, radially-oriented cylindrical shoulder 278. Shoulder 278 merges at annular outside corner 280 with a diametrally enlarged solid cylindrical body 282, which comprises surface 284. The diameter surface 284 is only slightly less than the diameter of surface 190, allowing axial and rotational displacement between surfaces 190 and 284. The small space between surfaces 190 and 284 is sealed so as to prevent flow of liquid thereacross by compressed O-ring 286 disposed in annular groove 191.

The proximal end of cylindrical body 282 comprises threads 288 at surface 284, which threads are sized, shaped, and configured so as to snugly and compatibly engage threads 192. The threaded portion 288 merges at annular outside corner 290 with a radially-directed shoulder or surface 292, which in turn merges at inside corner 294 with cylindrical segment 296. Cylindrical segment 296 is illustrated as being solid and as comprising an exterior cylindrical surface 298. Surface 296 is stepped at shoulder surface 300, the merger between surface 298 and surface 300 occurring at annular inside corner 302.

Shoulder surface 300 merges with annular knob surface 304 at outside annular corner 306. Annular surface 304 of knob 184 can comprise a surface texture and merges with blunt proximal end surface 308 at outside annular corner 310.

When the slit valve/control assembly 170 is positioned for use, in the manner illustrated in FIG. 1, the medical attendant manually rotates control knob 184 until blunt distal surface 274 is spaced a desired distance from the diaphragm 226 so that the slit 234 in the diaphragm 226 opens, in a downward direction, at precisely the desired net pressure or pressure differential threshold. The medical attendant may at any time vary the distance between the blunt surface 274 and the diaphragm 226, by rotation of the knob 184, to alter, as advisable and appropriate for the patient, the pressure differential threshold at which the slit 234 opens in a downward direction.

While not illustrated, it is to be appreciated that two valve assemblies 170 can be used in opposed relation (similar to the FIG. 4 and 5 arrangements) so that the pressure threshold for flow in either direction across the diaphragm 226 may be selectively varied by the medical attendant, as appropriate for the patient. Variations in the pressure differential threshold at which the slit 234 in diaphragm 226 opens is manually controlled by proper manipulation of knob 184 and does not require that the assembly or assemblies 170 be disconnected or disassembled.

Reference is now specifically made to FIG. 15 which, as mentioned above, depicts a diaphragm control/flow diverting slit valve assembly 172. By observation, it is seen that assembly 172 comprises previously described diaphragm 226 and end cap 176 and a slight variation of the cylindrical housings. Cylindrical housing 174' of FIG. 15 differs only from housing 174 of FIG. 14 that the boss 204 has been eliminated in housing 174 and the cylindrical wall 186 does not accommodate radially-directed liquid flow. Accordingly, the various parts and characteristics of diaphragm 226, cylindrical housing 174', and end cap 176 are numerated identically in FIG. 15 as in FIG. 14. Since these components were earlier described in conjunction with FIG. 14, no further description is needed in conjunction with FIG. 15.

Assembly 172 does not comprise control/diverter 182, previously described in conjunction with FIG. 14, but rather comprises a somewhat different diaphragm control/flow diverting member, generally designated 320. Control/diverter 320 is generally cylindrical and is stepped diametrally in a manner and for purposes explained below. Control/diverter 320 comprises a distal diametrally-reduced generally cylindrical portion 322. Portion 322 comprises a distal blunt flow-diverting end edge surface 324, which is generally parallel to the orientation of diaphragm 226. Surface 324 is circular and merges at annular outside corner 326 fixed with an exterior cylindrical surface 328. Generally cylindrical portion 322 defines an internal blind bore which ends with blunt, radially-directed interior wall surface 330. Surface 330 is circular and illustrated as being parallel to surface 324. Circular surface 320 merges at annular inside corner 332 with internal cylindrical surface 334. Cylindrical surface 334 is axially-directed and defines a hollow interior which functions as a flow path for liquid. Surfaces 324 and 334 comprise outside and inside surfaces of a cylindrical wall 336, which is interrupted by opposed apertures or orifices 338. Orifices 338 are illustrated as being of the same diameter and oriented so as to accommodate generally radially directed flow between the hollow chamber 340, defined by wall 334, and a distal chamber 342 disposed between distal cylindrical portion 322 of control/diverter 320, the interior surface 190 of cylindrical housing 174' and surface 232 of diaphragm 226.

Cylindrical portion 322 of control/diverter 320 merges at annular corner 344 with a radially-directed annular surface 346. Shoulder surface 346 merges, as one piece, at outside annular corner 348 with main cylindrical body 350. Main cylindrical body 350 comprises an outside generally cylindrical surface 352 as well as previously mentioned interior, chamber-defining surface 334. Body portion 350 is illustrated as being solid except for hollow chamber 340. Surface 352 comprises threads 354 at a proximal portion thereof. Threaded outside corner 356 merges with a radially-directed shoulder surface 358, which in turn merges at inside annular corner 360 with a diametrally reduced cylindrical surface 362, which comprises the outside of a cylindrical wall 364. The inside surface of wall 364 comprises previously mentioned surface 334. Annular wall 364 terminates in radially-directed blunt end edge surface 366, which merges at annular corner 368 with surface 362 and at corner 367 with surface 334.

Assembly 172, in use, is serviced by two flow tubes, one of which is force-fit or compression-secured over boss 254 and the other of which is compression-fit over surface 362. Flow between the two tubes occurs along the passageway defined by surface 260 of boss 254, through cavity 342 and along chamber 340. Flow across the diaphragm 226 into and from the cavity 342 is along surface 324, across surface 328, through apertures or orifices 338 and along chamber 342.

The spacing between the diaphragm 226 and surface 324 can be adjusted by manual rotation of the control/diverter 320 to create a pressure differential threshold response necessary to open slit 234 precisely as desired by the medical supervisor. Rotation of the control/diverter 320 can include counter rotation of the liquid-communicating tubing force fit upon surface 362 or, in the alternative, tubing can be temporarily removed from surface 362, the control/diverter 320 rotated and the tubing force-fit over surface 362 once more. Of course, adequate medical care must be taken to insure that such a procedure does not create inappropriate medical circumstances and risks for the patient.

Two valve assemblies 172 can be used in opposed relation so that the pressure threshold for flow in either direction across the diaphragm may be selectively varied in the manner explained above.

The invention may be embodied in other specific forms without departing from the spirit of the central characteristics thereof. The present embodiments therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A medical respiratory flow control assembly comprising:

a first tube comprising a hollow interior for placement, at a distal end thereof, in a patient, the first tube comprising a ventilation tube placed in part in the respiratory system of the patient;

a source of respiratory gas under pressure disposed external of the patient by which a first gaseous pressure is obtained;

a second hollow tube disposed external of the patient, a proximal interior of the second hollow tube being in communication with the source and the pressure there obtained;

a valve housing interposed between the first and second hollow tubes external of the patient, a proximal part of the valve housing being in communication with the interior of the second hollow tube, at a distal end thereof, and the pressure obtained from the source, a distal part of the valve housing being in communication with the hollow interior of the first tube and via the hollow of the first tube in communication with a patient-determined exhalation pressure;

a slit valve disposed within the valve housing between the source pressure and the patient-determined exhalation pressure, the valve housing comprising a flexible normally closed bi-directionally pressure-responsive slit diaphragm selectively accommodating gaseous flow across the slit diaphragm in either direction between the interiors of the two hollow tubes;

an adjustment member movingly disposed within the valve housing at one side of the diaphragm and selectively space-coordinated with the slit diaphragm to selectively restrict the permitted flexure of the slit diaphragm to vary the threshold required to open the slit diaphragm in the direction of the adjustment member.

2. A medical fluid flow assembly according to claim 1 wherein the pressure differential during commencement of exhalation is sufficient to open the slit diaphragm in a direction away from the patient, but insufficient to keep the slit diaphragm open before the end of exhalation so that some gas is retained in the lungs at the commencement of the next inhalation phase.

3. A medical fluid flow control assembly comprising:

a first tube comprising a hollow interior for placement, at a distal end thereof, in a patient;

a source of fluid disposed external of the patient by which a first pressure is obtained;

a second hollow tube disposed external of the patient, a proximal interior of the second hollow tube being in communication with the fluid source and the pressure there obtained;

a valve housing interposed between the first and second hollow tubes external of the patient, a proximal part of the valve housing being in communication with the interior of the second hollow tube, at a distal end thereof, and the pressure obtained from the fluid source, a distal part of the valve housing being in communication with the hollow interior of the first tube and via the hollow of the first tube in communication with a patient-determined pressure;

a slit valve disposed within the valve housing between the fluid source pressure and the patient-determined pressure, the valve housing comprising a flexible normally closed bi-directionally pressure-responsive slit diaphragm selectively accommodating liquid flow across the slit diaphragm in either direction between the interiors of the two hollow tubes;

an adjustment member movingly disposed within the valve housing at one side of the diaphragm and selectively space-coordinated with the slit diaphragm to selectively restrict the permitted flexure of the slit diaphragm to vary the threshold required to open the slit diaphragm in the direction of the adjustment member;

another adjustment member movingly disposed within the valve housing on the other side of the slit diaphragm, the second adjustment member being selectively in spaced coordination with the slit diaphragm to selectively restrict the permitted flexure of the slit diaphragm to vary the pressure differential threshold required to open the slit diaphragm in the direction.

4. An adjustable two-way valve structure for controlling fluid flow comprising:

a housing comprising a proximal fluid flow port, a distal fluid flow port, and an interior accommodating selective fluid flow therethrough;

a displaceable, pressure-responsive slit diaphragm transversely disposed within the hollow interior of the housing between the proximal and distal flow ports, the slit diaphragm comprising a yieldable diaphragm in which at least one slit is centrally disposed and flexed by a predetermined fluid pressure differential across the diaphragm;

a first adjustment member movingly disposed within the housing, the adjustment member comprising a hollow interior and a contact surface, the contact surface being juxtaposed the slit diaphragm by a selectively variable distance to alter a threshold pressure differential at which the slit diaphragm opens to accommodate fluid flow across the diaphragm;

a second adjustment member movingly disposed within the housing and disposed on the opposite side of the diaphragm as the first adjustment member, the second adjustment member being juxtaposed the slit diaphragm by a selectively variable distance to alter a threshold pressure differential at which the slit diaphragm opens in the direction of the second adjustment member for fluid flow.

5. A valve structure according to claim 4 wherein the second adjustment member further comprises the threads of the second and the housing further comprises threads the threads of the second adjustment member and of the housing being threadedly engaged to permit the selective relocation of the second adjustment member in respect to the housing and the diaphragm to vary the pressure differential threshold at which the slit diaphragm opens toward the second adjustment member.

6. A valve structure according to claim 4 wherein a seal is interposed between the housing and the second adjustment member to prevent fluid leakage.

7. A valve structure according to claim 4 wherein an O-ring is interposed between the housing and the second adjustment member to prevent fluid leakage.

8. An adjustable two-way valve structure for controlling gaseous flow comprising:

a housing comprising a proximal gaseous flow port, a distal fluid flow port, and an interior accommodating selective gaseous flow therethrough;

a displaceable, pressure-responsive slit diaphragm transversely disposed within the hollow interior of the housing between the proximal and distal flow ports, the slit diaphragm comprising a yieldable diaphragm in which at least one slit is centrally disposed and flexed by a predetermined gaseous pressure differential across the diaphragm;

an adjustment member movingly disposed within the housing, the adjustment member comprising a hollow interior and a contact surface, the contact surface being juxtaposed the slit diaphragm by a selectively variable distance to alter a threshold pressure differential at which the slit diaphragm opens to accommodate gaseous flow across the diaphragm.

9. A method of selectively controlling medical gaseous flow to and from a patient comprising the steps of:

placing a distal end of a cannula indwelling within the respiratory system of the patient so that a hollow interior of the cannula is subject to a patient-created gaseous pressure;

connecting a distal end of an outdwelling valve housing to a proximal end of the cannula for selective internal gaseous communication along a predetermined path within the housing;

causing a normally closed flexible slit diaphragm to be securely interposed across the flow path within the housing so that one side of the slit diaphragm is subjected to the patient-created gaseous pressure;

causing a movable adjustment member to be moveably disposed in respect to the valve housing juxtaposed the diaphragm;

creating gaseous pressure on a second side of the diaphragm to thereby cause gaseous pressure differential across the diaphragm to exist;

adjusting the magnitude of gaseous pressure differential across the diaphragm required to flex and open the diaphragm to accommodate medical gaseous flow across the diaphragm by selectively moving the adjustment member relative to the diaphragm to vary the space between the adjustment member and the diaphragm.

10. A method of adjusting the pressure differential across a slit valve necessary to open the valve to accommodate selective fluid flow across the slit valve comprising the steps of:

providing a housing having a flow path therethrough;

causing a normally closed flexible slit diaphragm having first and second sides to be securely interposed across the flow path within the housing;

causing an adjustment member to be moveably and adjustably disposed within the housing adjacent to the first side of the diaphragm;

causing a second adjustment member to be moveably disposed within the housing adjacent to the second side of the diaphragm;

creating a fluid pressure differential across the diaphragm;

when a pressure differential of predetermined magnitude occurs sufficient to flex the diaphragm, selectively physically limiting the extent to which the diaphragm is permitted to flex in the direction of either adjustment member by selectively engaging either adjustment member by the flexed diaphragm.

11. A method according to claim 10, further comprising the steps of:

providing threads on an external surface of the second adjustment member;

providing threads on an internal surface of the housing;

threadedly engaging the housing threads with the second adjustment member threads;

selectively threadedly moving the second adjustment member relative to the diaphragm by selectively rotating the second adjustment member relative to the housing.

12. A medical flow control assembly comprising:

a cannula comprising a hollow interior for placement, at a distal end thereof, in a patient;

a source of fluid disposed external of the patient;

a hollow tube disposed external of the patient, a proximal end of the hollow of the tube being in fluid communication with the source;

a slit diaphragm interposed between a distal end of the hollow tube and a proximal end of the cannula, a proximal side of the slit diaphragm being subjected to fluid pressure within the hollow interior of the tube and a distal side of the slit diaphragm being subjected to fluid pressure within the hollow of the cannula, the slit diaphragm flexing to an open condition when a pressure differential of a predetermined magnitude occurs;

at least one adjustable interference member located immediately adjacent the slit diaphragm a variable distance whereby variation in the location of the interference member in respect to the diaphragm alters when and the extent to which the slit diaphragm opens toward the interference member, the at least one adjustable interference member comprising two adjustable members, one disposed on each side of the slit diaphragm.

* * * * *